United States Patent
Hodgson

(10) Patent No.: US 7,014,634 B2
(45) Date of Patent: Mar. 21, 2006

(54) ANESTHETIC DELIVERY DEVICE

(76) Inventor: David S. Hodgson, 2700 Brittany Ter., Apt. 1, Manhattan, KS (US) 66502

( * ) Notice: Subject to any disclaimer, the term of this patent is extended or adjusted under 35 U.S.C. 154(b) by 0 days.

(21) Appl. No.: 10/899,889

(22) Filed: Jul. 26, 2004

(65) Prior Publication Data

US 2005/0020999 A1    Jan. 27, 2005

Related U.S. Application Data

(60) Provisional application No. 60/489,845, filed on Jul. 24, 2003.

(51) Int. Cl.
*A61M 31/00* (2006.01)
(52) U.S. Cl. ............. 604/512; 128/200.14; 128/204.14
(58) Field of Classification Search ........... 128/200.16, 128/202.13, 206.29, 898, 200.11, 200.13–200.14, 128/200.18, 200.21–200.23, 204.13–204.14; 604/181, 264, 183–185, 313, 2, 3, 289, 290, 604/246, 140, 141, 21; 239/361, 343, 346, 239/351

See application file for complete search history.

(56) References Cited

U.S. PATENT DOCUMENTS

| | | | | | |
|---|---|---|---|---|---|
| 2,086,588 | A | * | 7/1937 | Tobin et al. | 128/204.13 |
| 3,794,027 | A | * | 2/1974 | Johnson | 128/204.13 |
| 3,807,635 | A | * | 4/1974 | Platt | 239/726 |
| 5,240,151 | A | * | 8/1993 | Worm | 222/318 |
| 5,622,167 | A | * | 4/1997 | Pinosky | 128/207.14 |
| 2003/0073976 | A1 | * | 4/2003 | Brushey | 604/525 |

* cited by examiner

*Primary Examiner*—Nicholas D. Lucchesi
*Assistant Examiner*—Laura A. Bouchelle
(74) *Attorney, Agent, or Firm*—Cochran Freund & Young LLC; William W. Cochran

(57) ABSTRACT

Disclosed is a vapor wand for administering inhalation anesthesia to wild animals. The wand has a fibrous wick that absorbs liquid anesthetic inserted by a syringe through a distal end cap and/or a leur fitting. Holes are spaced around the distal end of the wand so that movement of the air pump handle causes vaporized anesthetic to be dispensed through the holes.

4 Claims, 3 Drawing Sheets

ANESTHETIC DELIVERY DEVICE

CROSS REFERENCE TO RELATED APPLICATIONS

This application claims benefit of and priority to U.S. Provisional Patent Application Ser. No. 60/489,845 entitled "Novel Anesthetic Delivery Device" by David Hodgson, filed Jul. 24, 2003, the entire contents of which are specifically incorporated herein by reference for all it discloses and teaches.

BACKGROUND OF THE INVENTION

Exotic wild animals and fractious, aggressive pets are often presented in cages for treatment by veterinarians. Handling these animals in a manner that is both safe to the veterinarian and humane for the animal may be impossible without anesthesia. It is important to minimize struggling and excessive fright to the animal since prolonged excitation can disturb the circulatory and metabolic state of the animal and induce a degree of shock. However, attempts to anesthetize a struggling wild animal or fractious pet presents safety problems in addition to enhancing the likelihood of an abnormal response. These points are particularly pertinent to the restraint and anesthesia of wild animals.

By definition tranquilizers produce psychological calming of anxiety without physiological depression or clouding of consciousness. However, when tranquilizers are used to produce manageability, high doses are usually necessary which may result in ataxia, variable response to stimulation and cardiorespiratory depression. Cardiovascular depression may be severe and, if followed by a general anesthetic, the combination may lead to severe hypotension.

Tranquilizers do not exert hypnotic or analgesic affects. Increasing the dose does not produce greater sedation, even though the psychological depressant affects are magnified.

The psychological state of the animal prior to administration of tranquilizers may markedly affect the degree of sedation achieved. Animals that are vicious, intractable and in a state of excitation may not become manageable, except with very high (incapacitating) doses, therefore it is often preferred to treat these animals with an anesthetic instead of tranquilizers.

Dissociative anesthetics produce a state of chemical restraint and anesthesia characterized by a form of muscle rigidity and an apparent dissociation of the mind from the external environment. The eyes remain open; various reflexes, including the blinking reflex remain intact. Adequate respiration is normally maintained, an increase in heart rate and blood pressure frequently occurs. While the widest use of dissociative anesthetic agents is probably with primates and felines, they have also been used in most other mammalian species as well as birds and reptiles.

Currently, these dissociative anesthetics and tranquilizers are administered via a dart delivered from a blowgun or syringe pole. Problems associated with darts are numerous. The dart must enter muscle tissue and fully discharge to deliver the calculated dose of drugs. Occasionally darts miss the animal entirely or do not discharge the drug into muscle tissue. Inadvertent movement of the animal may allow the dart to hit the animal's eye or other organ that may produce damage and harm. With injectable drugs it is difficult to estimate the amount of drug to use. An overdose may produce death and an under dose may produce more agitation and excitement. Some animals, especially primates that have been darted in the past are very apprehensive when they know that they are to be darted again. The time from darting to restraint of the patient is very unpredictable. Darting devices used by unskilled operators can produce more damage than benefits.

Inhalant anesthetics delivered in sufficient quantity over a short period of time give a relatively rapid onset and rapid recovery after the inhalation anesthetic is discontinued. They can be administered with a high degree of controllability over anesthetic depth and duration through the manipulation of drug dose, rate of vaporization, and cessation of administration when the desired effect is produced on the animal. To date, however, specialized, expensive vaporizers and oxygen equipment has been required to use inhalant anesthetics. These devices are very expensive and delivery of anesthetic to large cages and chambers is very prolonged before effects on the animal are seen.

Monitoring the dosage of inhalant anesthetic is important. Differences in anesthetic solubility determine the speed with which gas concentration builds up in the arterial blood. As highly soluble gases require more time to build up a significant concentration in the blood, they result in a more prolonged induction and recovery. The reverse is true of the highly insoluble gases which are therefore more controllable as their blood concentration can be rapidly changed; however, for this reason they are more hazardous and require quantitative methods to govern their delivery in safe concentrations.

Currently, inhalant anesthetics can be administered by means of a simple nose cone for the performance of short procedures or via a mask or endotrachial tube connected to a vaporizer. Numerous apparati have been devised for these purposes, but none of these can be effectively used to treat the excited or vicious animal before removing it from its cage. The current way to deliver anesthetics to cages is to flow oxygen through an expensive precision vaporizer. This method consumes large volumes of oxygen and volatile liquid anesthetics. For animals in large chambers, a prolonged period of time is necessary to induce an anesthetic state. This method is not adaptable to use in the field except with a lot of heavy, complex, and expensive equipment.

Accordingly, what is needed in the art is a simple, inexpensive, transportable device and method to safely anesthetize wild or otherwise vicious animals while they are in their transport cages.

BRIEF SUMMARY OF THE INVENTION

The present invention solves the prior art problems mentioned above and provides a distinct advance in the state of the art. In particular, through the present invention, apparatus and methods are provided which allow the application of inhalation anesthesia to wild animals or fractious domestic pets before they are removed from their transport cages. The apparatus and method are easy to use, relatively inexpensive to produce, transportable to the field, safe and effective.

The present invention may therefore comprise an apparatus for use in anesthetizing animals in cages comprising: a metal tube having a tube wall and a plurality of holes formed in the tube wall in a spaced apart relationship around the metal tube and along a distal portion of the metal tube; a wick disposed in the metal tube, the wick made of fibrous material that is adapted to absorb liquid anesthetic; an end cap disposed in the distal end of the metal tube, the end cap having an opening for delivering liquid anesthesia, using a needle, through the end cap to the wick; a flexible tube connected to a proximal end of the metal tube that is capable of delivering air to and from the metal tube; an air pump that pumps air into and evacuates air from the metal tube by actuation of a pump handle to cause vaporization of the liquid anesthesia on the wick.

The present invention may further comprise a method of administering anesthesia to animals in a cage using a vapor wand comprising: injecting liquid anesthetic through an end cap in the vapor wand using a needle that is adapted to fit in an opening in the end cap so as to deliver the liquid anesthetic to a fibrous wick, the vapor wand having a metal tube with the end cap attached to a distal end of the metal tube, the metal tube having a plurality of holes disposed along a distal portion of the metal tube, the fibrous wick disposed in the metal tube so as to absorb the liquid anesthesia injected through the end cap; attaching a proximal end of the metal tube to a plastic tube; attaching the plastic tube to an air pump; activating the air pump to cause air to flow through the metal tube and vaporize the liquid anesthetic so that vaporized liquid anesthetic is discharged from the vapor wand through the holes.

Embodiments of the invention offer several advantages over the current art. For example, the apparatus is appropriate for field, clinic or hospital use thus giving it wide applicability. No electricity or compressed gases or oxygen is needed to power the device. It is therefore, a unique apparatus and method for delivering inhalant anesthetics in the field. The apparatus is easy to operate, inexpensive and can be produced in several sizes to accommodate a wide variety of clinical and research applications. The method is easy to understand and implement while producing controllable and reliable results. In addition, the volume of anesthetic used is much smaller than that used when flowing gas through a calibrated vaporizer resulting in additional cost savings.

DETAILED DESCRIPTION OF THE INVENTION

Figure 1:
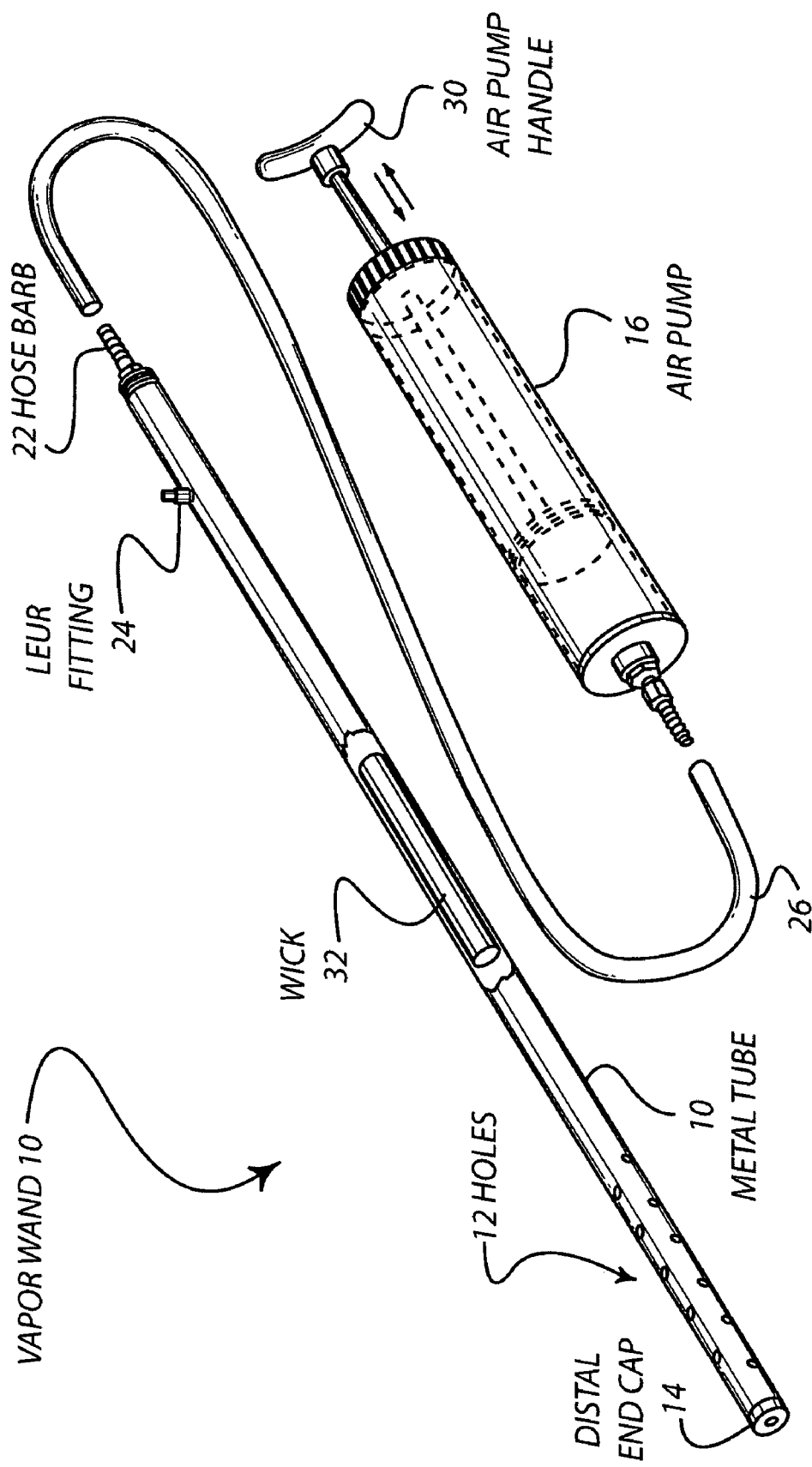
FIG. 1 is a pictorial view of the vapor wand apparatus, shown with the parts broken away to illustrate assembly of the pieces.

The following examples set forth various embodiments of the present invention. It is to be understood, however, that these examples are provided by way of illustration and should not be taken as limiting the overall scope of the invention.

Materials and Methods

A vapor wand was constructed of 1.9 cm OD copper tube 10 which is 75 cm in length with multiple 0.6 cm holes 12 in the distal 20 cm portion of the tube. A distal end-cap with hole 14 is fitted to introduce liquid isoflurane (ISO) via a hypodermic syringe into a full-length cotton wick 32. The proximal end is fitted with a 0.6 cm hose barb 22 and a female leur fitting 24 to allow additional ISO administration.

The vapor wand 10 is constructed of a metallic (stainless steel, brass, or copper) tube 10 with multiple holes 12 in the distal end. A distal end-cap 14 with injection hole is fitted to introduce inhalant anesthetics in the liquid form into the vapor wand via a hypodermic syringe (not shown) into a full-length fibrous wick 32 that may be made of cotton. The proximal end is fitted with a hose barb 22 and female leur fitting 24 to allow additional anesthetic administration. The air pump 16, or other recirculation device, is connected to the hose barb 22 via flexible tubing 26.

The apparatus can be constructed in a variety of sizes to accommodate different cage sizes. The appropriate size of the apparatus is determined by the amount of anesthetic that is initially loaded onto the cotton wick 32 in order to achieve the desired target anesthetic concentration. For small volumes a smaller wand with a shorter wick can be used. Similarly, for cages with large volumes, a larger wand with longer wick can be used.

Embodiments of the present invention allow a desired amount of anesthesia to be delivered to caged animals in order to temporarily immobilize the animal, while adequate respiration and heart rate are maintained so that the animal can be safely and humanely removed from the cage for subsequent treatment. Formulas have been developed, depending on cage volume, to produce a target anesthetic concentration that is shown in FIGS. 2 and 3.

Upon presentation of the animal in a cage, the cage is measured and the volume of the cage is calculated. The cage is then enclosed in a heavy, close fitting plastic bag. After injecting the desired volume of anesthetic into the wick 32 of the vapor wand, the distal end of the vapor wand is introduced through a small hole cut into the plastic bag. The opening of the bag is sealed around a transparent window to facilitate ongoing observation of the animal. The proximal end of the vapor wand remains outside of the cage. A gas tight air pump 16, or other circulating device, is then attached to the hose barb 22 and is pumped using air pump handle 30 to cycle cage gas back and forth through the vapor wand to enhance vaporization of the liquid anesthetic in the wick 32. The more frequent the cycling of the syringe, the faster the liquid is vaporized and the faster the animal becomes anesthetized.

The device illustrated in FIG. 1 was used to anesthetize different species and sizes of animals, including domestic cats, dogs and mandrills (small baboon). Cage volumes ranged from 28 to 275 liters (1708 to 16780 cubic inches). Liquid volume of isoflurane (ISO) was calculated to produce a target concentration of five percent if complete vaporization occurred. The speed of induction time varied directly with cage volume. Induction times ranged from 2.07 to 7.5 minutes. At completion of induction of anesthesia and immobilization, the bag was rapidly opened and a mask was fitted on the patient's nose and attached to an anesthetic circuit to maintain anesthesia.

Figure 2:
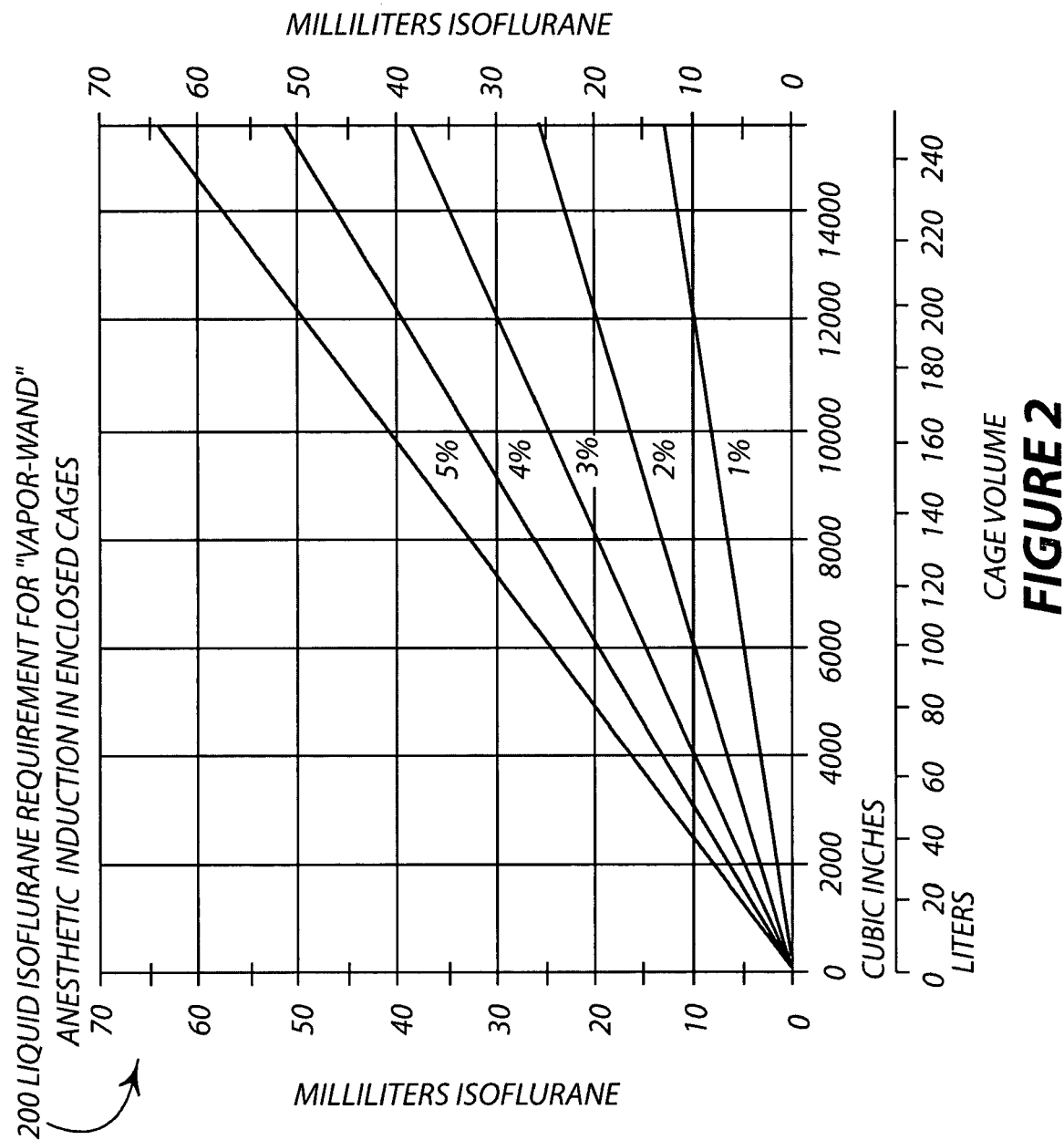
FIG. 2 is a graph illustrating the method for determining the amount of anesthetic to use to achieve the desired concentration as determined by cage volume for cage volumes ranging from zero to 16,000 cubic inches.
Figure 3:
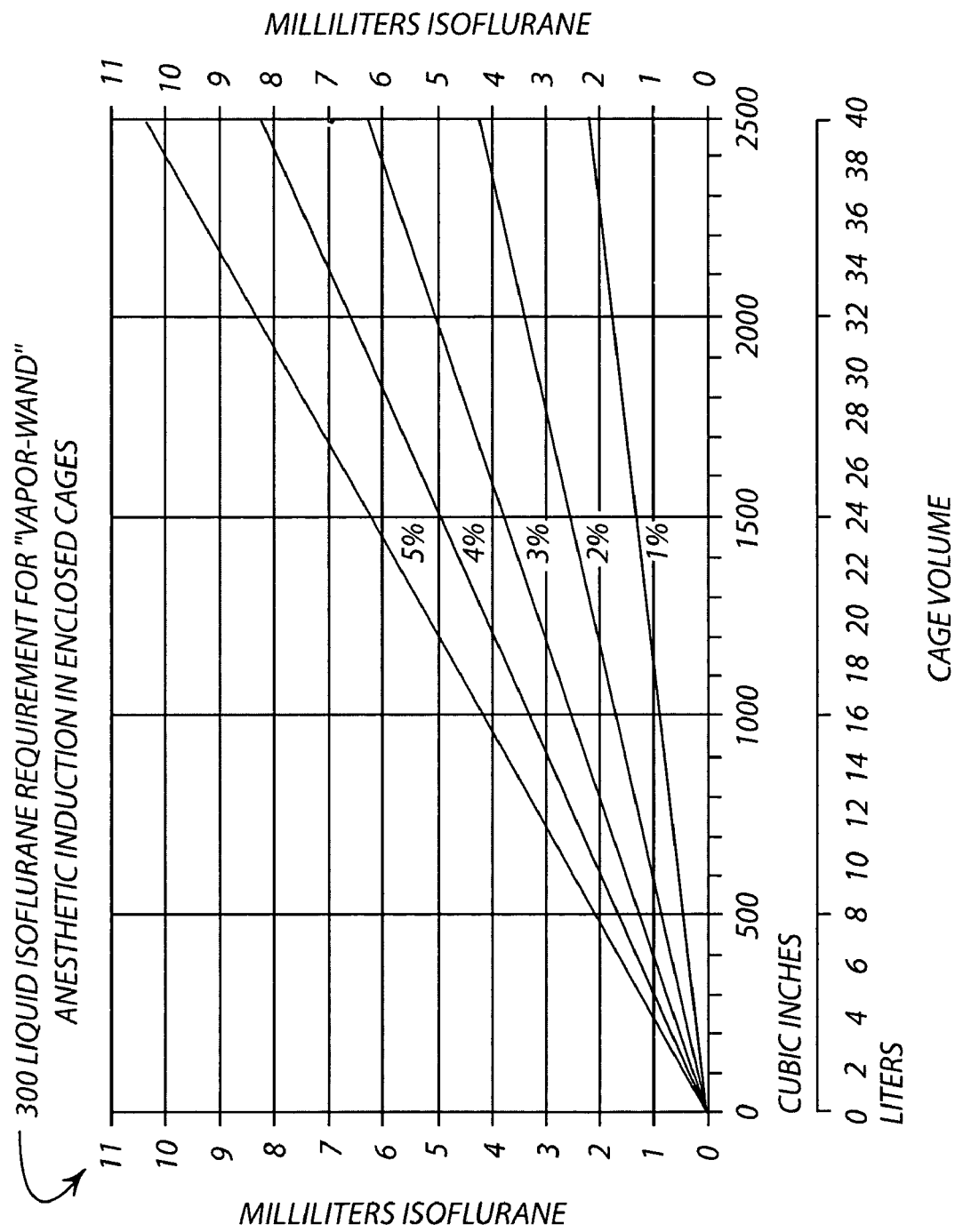
FIG. 3 is a graph illustrating the method for determining the amount of anesthetic to use to achieve the desired concentration as determined by cage volume for cage volumes ranging from zero to 2,500 cubic inches.

FIG. 2 is a graph 200 illustrating the liquid isoflurane requirements for anesthetic induction of animals in enclosed cages. The graph shows the percentage of isoflurane vapor plotted for cage volumes from 0 to over 240 liters versus the amount of isoflurane in milliliters.

FIG. 3 is a graph 300 illustrating the liquid isoflurane requirements for anesthetic induction of animals in enclosed cages. The graph shows the percentage of isoflurane vapor plotted for cage volumes varying from 0 to 40 liters versus the amount of isoflurane in milliliters.

EXAMPLE 1

This example pertains to a Ferel cat presented by a police department animal control officer. The cage containing the cat measured 12"×12"×21" with a volume 3024 cubic inches. The target concentration of isoflurane vapor equaled five percent. The cage was placed inside a plastic bag and was then sealed around a small transparent window. The vapor wand was loaded with 12.4 ml isoflurane liquid and inserted through a small hole that was cut into the bag. The air pump was manually pumped to cycle cage gas back and forth through the vapor wand to enhance vaporization of the liquid anesthetic in the wick.

Results

Induction time to complete anesthesia was two minutes and three seconds. The induction was very smooth, with no adverse movements or responses.

EXAMPLE 2

A Mandrill (small baboon) was presented in a cage which measured 22"×32"×24" with a volume of 16,896 cubic inches. The target concentration of isoflurane vapor equaled five percent. The cage was placed inside a plastic bag and was then sealed around a small transparent window. The vapor wand was loaded with 76 ml isoflurane liquid and inserted through a small hole that was cut into the bag. The air pump was manually pumped to cycle cage gas back and forth through the vapor wand to enhance vaporization of the liquid anesthetic in the wick.

Results

Induction time to complete immobility and a moderate plane of anesthesia was six minutes and eighteen seconds. The induction was very smooth. The animal was quiet with no struggling.

Conclusion

As described above, the vapor wand can be used to safely and effectively anesthetize a variety of aggressive animals while they are in their cages. It should be understood that the implementation shown is illustrative and should not be considered as limiting in any way the scope of the invention. For example, the apparatus and method can be used to anesthetize animals other than those shown. The apparatus can be constructed in varying sizes to accommodate both large and small cages, the size of the apparatus being dependent on the amount of liquid anesthetic required to achieve the target anesthetic concentration. Thus, the apparatus and method of use of the apparatus are advancements over the current art, providing an inexpensive, reliable, portable device for anesthetizing animals presented in cages for treatment.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An apparatus for use in anesthetizing animals in cages comprising:
    a metal tube having a tube wall and a plurality of holes formed in said tube wall in a spaced apart relationship around said metal tube and along a distal portion of said metal tube;
    a wick disposed in said metal tube, said wick made of fibrous material that is adapted to absorb liquid anesthetic;
    an end cap disposed in said distal end of said metal tube, said end cap having an opening for delivering liquid anesthesia, using a needle, through said end cap to said wick;
    a flexible tube connected to a proximal end of said metal tube that is capable of delivering air to and from said metal tube; and
    an air pump that pumps air into and evacuates air from said metal tube by actuation of a pump handle to cause vaporization of said liquid anesthesia on said wick.

2. The apparatus of claim 1 further comprising:
    a luer adapter attached to a proximal end of said metal tube to allow additional liquid anesthetic to be inserted in said metal tube using said syringe.

3. A method of administering anesthetic to animals in a cage using a vapor wand comprising:
    injecting liquid anesthetic through an end cap in said vapor wand using a needle that is adapted to fit in an opening in said end cap so as to deliver said liquid anesthetic to a fibrous wick, said vapor wand having a metal tube with said end cap attached to a distal end of said metal tube, said metal tube having a plurality of holes disposed along a distal portion of said metal tube, said fibrous wick disposed in said metal tube so as to absorb said liquid anesthetic injected trough said end cap;
    attaching a proximal end of said metal tube to a plastic tube;
    attaching said plastic tube to an air pump; and
    activating said air pump to cause air to flow through said metal tube and vaporize said liquid anesthetic so that vaporized liquid anesthetic is discharged from said vapor wand through said holes.

4. The method of claim 3 further comprising;
    placing said cage in a plastic bag; and
    placing said distal end of said vapor wand in said plastic bag prior to discharge of said vaporized liquid anesthetic.

* * * * *